United States Patent [19]

Niimura et al.

[11] Patent Number: 5,324,740
[45] Date of Patent: Jun. 28, 1994

[54] AZOLE DERIVATIVES, PHARMACEUTICAL COMPOSITIONS CONTAINING THE SAME, AND METHOD FOR TREATING MYCOSIS AND ESTROGEN-DEPENDENT DISEASES

[75] Inventors: Koichi Niimura, Saitama; Yuko Ikeda, Chiba; Akira Kato; Takao Ando, both of Tokyo, all of Japan

[73] Assignee: Kureha Chemical Industry Co., Ltd., Japan

[21] Appl. No.: 67,052

[22] Filed: May 26, 1993

[30] Foreign Application Priority Data

Jun. 6, 1992 [JP] Japan .................. 4-171731

[51] Int. Cl.$^5$ .................. A61K 31/415; C07D 409/06; C07D 405/06; C07D 403/06
[52] U.S. Cl. .................. 514/397; 548/314.7; 548/315.1; 548/315.4
[58] Field of Search .................. 548/314.7, 315.1; 514/397

[56] References Cited

U.S. PATENT DOCUMENTS 4,735,910  4/1988  Hirsch et al. .................. 514/361

FOREIGN PATENT DOCUMENTS 0023756  2/1981  European Pat. Off. .
0061910  10/1982  European Pat. Off. .
0267778  5/1988  European Pat. Off. .
0294222  12/1988  European Pat. Off. .
2180236A  3/1987  United Kingdom .

*Primary Examiner*—Patricia L. Morris
*Attorney, Agent, or Firm*—Parkhurst, Wendel & Rossi

[57] ABSTRACT

Azole derivatives (including stereoisomers and pharmaceutically acceptable salts) of the formula:

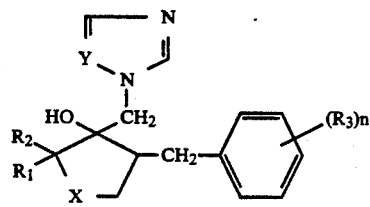

wherein $R_1$ and $R_2$ each are H or $C_1$–$C_4$ alkyl; $R_3$ is H, OH, CN, halogen, haloalkyl, $C_1$–$C_4$ alkyl or phenyl, and if there are two or more $R_3$ groups, such $R_3$ groups may be the same or different; n is an integer from 0 to 5; Y is N or CH; and X is O, S or NH have antimycotic and aromatase inhibitory activities. Compositions containing the azole derivatives and a method of treating mycosis and estrogen-dependent diseases by administering effective quantities of the azole derivatives are also disclosed.

4 Claims, No Drawings

AZOLE DERIVATIVES, PHARMACEUTICAL COMPOSITIONS CONTAINING THE SAME, AND METHOD FOR TREATING MYCOSIS AND ESTROGEN-DEPENDENT DISEASES

BACKGROUND OF THE INVENTION

1. Field of the Invention

The present invention relates to azole derivatives, to pharmaceutical compositions containing the same, and to a method for treating mycosis or estrogen-dependent diseases.

2. Description of the Related Art

In recent years, the number of opportunistically-infected patients with low immunologic resistance has been increasing with the medical progress.

Opportunistically-infectious mycosis profundus, such as Candidiasis, Aspergillosis, and Cryptococcosis, is occurring in such patients at a high rate, and effective countermeasures for such mycosis are becoming more and more difficult to achieve.

Therefore, research for developing a medicine superior to the conventional antimycotic agents is being actively conducted. Further, research for developing aromatase inhibitors is being conducted also.

SUMMARY OF THE INVENTION

An object of the present invention is to provide novel azole derivatives useful for treating mycosis or for use as aromatase inhibitors.

The present inventors have found that novel azole derivatives having a heterocyclopentane ring have low toxicity and high antimycotic activity per os, as well as having high aromatase inhibitory activity.

The present invention is based on such findings.

According to a first aspect of the present invention, there are provided azole derivatives of the formula (I):

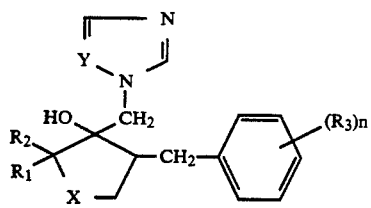

and stereoisomers thereof, wherein $R_1$ and $R_2$ respectively are H or $C_1$-$C_4$ alkyl; X is O, S, or NH; $R_3$ is H, OH, CN, halogen, haloalkyl, $C_1$-$C_4$ alkyl, or phenyl, and if there are two or more $R_3$ groups, such $R_3$ groups may be the same or different; n is an integer from 0 to 5; and Y is N or CH, and pharmaceutically acceptable salts thereof.

According to a second aspect of the present invention, there are provided pharmaceutical compositions containing the azole derivatives of formula (I).

According to a third aspect of the present invention, there is provided a method of using the azole derivatives of formula (I) to treat mycosis and estrogen-dependent diseases.

The novel azole derivatives of the present invention have low toxicity, antimycotic activity even by oral administration, and aromatase inhibitory activity.

DESCRIPTION OF THE PREFERRED EMBODIMENTS

The compounds according to the present invention are compounds of formula (I):

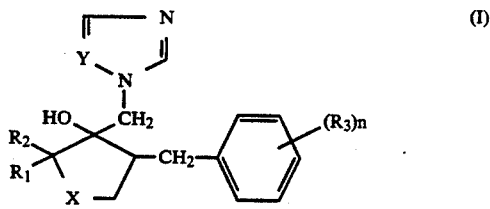

and stereoisomers thereof; wherein $R_1$ and $R_2$ each are H or $C_1$-$C_4$ alkyl; X is O, S, or NH; $R_3$ is H, OH, CN, halogen, haloalkyl, $C_1$-$C_4$ alkyl or phenyl, and if there are two or more $R_3$ groups, such $R_3$ groups may be the same or different; n is an integer from 0 to 5; and Y is N or CH, and pharmaceutically acceptable salts thereof.

The novel compounds of formula (I) can be prepared by:

a) reacting compounds of formula (V)

wherein $R_1$ and $R_2$ respectively are H or $C_1$-$C_4$ alkyl; X is O, S, or NH; and R is alkyl, with compounds of formula (IV')

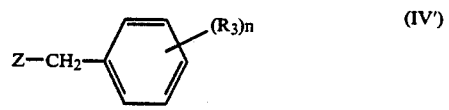

wherein $R_3$ is H, OH, CN, halogen, haloalkyl, $C_1$-$C_4$ alkyl or phenyl, and if there are two or more $R_3$ groups, such $R_3$ group may be the same or different; Z is a leaving group; and n is an integer from 0 to 5, thereby obtaining compounds of formula (IV)

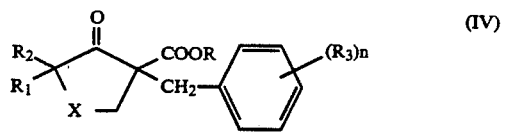

wherein R, $R_1$, $R_2$, $R_3$, X, and n have the same meaning as described in formulae (V) and (I), b) subjecting the compounds of formula (IV) to decarboxylation, thereby obtaining compounds of formula (III):

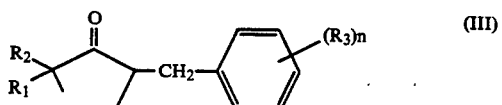

wherein $R_1$, $R_2$, $R_3$, X, and n are defined the same as in formulae (V) and (I), c) reacting the compounds of formula (III) with sulfur ylide, thereby obtaining compounds of formula (II):

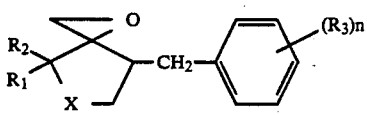

wherein $R_1$, $R_2$, $R_3$, X, and n have the same meaning as in formulae (V) and (I), and d) reacting the compounds of formula (II) with compounds of formula (II'):

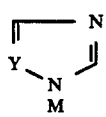

wherein Y is N or CH; and M is a metal ion, thereby obtaining the compounds of formula (I).

In formulae (I), (II), (II'), (III), (IV), (IV') and (V), the $C_1$–$C_4$ alkyl of $R_1$, $R_2$, and $R_3$ includes methyl, ethyl, straight-chain or branched-chain propyl, or straight-chain or branched-chain butyl.

Halogen of $R_3$ and Z includes, for example, Cl, Br, I, and F.

Alkyl of R preferably is a $C_1$–$C_4$ alkyl, for example, methyl, ethyl, straight-chain or branched-chain propyl, or straight-chain or ranched-chain butyl.

Haloalkyl is alkyl substituted with halogen such as Cl, Br, I, or F.

The metal ion of formula (II') includes Na, K, and other monovalent metal ions.

Examples of suitable diluents which can be used in a series of reactions in steps (a), (b), (c), and (d) for preparing the azole derivatives of formula (I) are: hydrocarbons, such as benzene, toluene, xylene, and hexane; halohydrocarbons, such as methylene chloride, chloroform, and carbon tetrachloride; alcohols, such as methanol, ethanol, and isopropanol; ethers such as diethyl ether, diisopropyl ether, tetrahydrofuran, and dioxane; acetonitrile; acetone; dimethylformamide; dimethyl sulfoxide; and ethyl acetate.

The reactions in steps (a), (b), (c), and (d) may be carried out in the presence of a base or an acid in addition to the above-mentioned diluent.

Examples of the base that can be used herein are: alkali metal carbonates, such as sodium carbonate and potassium carbonate; alkali metal hydroxides, such as sodium hydroxide and potassium hydroxide; alkali metal alcoholates, such as sodium methylate, sodium ethylate and potassium tertiary butyrate; alkali metal hydrides such as sodium hydride and potassium hydride; alkyl compounds of alkali metals, such as n-butyl lithium; and other bases, such as triethylamine and pyridine.

Examples of the acid used in the described process are: inorganic acids, such as hydrochloric acid, hydrobromic acid, hydroiodic acid, and sulfuric acid; and organic acids such as formic acid, acetic acid, butyric acid, and p-toluenesulfonic acid.

The cyclopentanone carboxylate derivatives of formula (V) used as a starting material in step (a) can be obtained by the method disclosed by M. A. Gianturco in Tetrahedron, 20, 1763, 1964.

In step (a):

The cyclopentanone carboxylate derivatives of formula (V) are substituted by a desirable benzyl group to obtain the cyclopentanone carboxylate compounds of formula (IV). The compounds of formula (V) are dissolved in the diluent above and, if necessary, in the presence of a base, reacted with benzyl derivatives.

The reaction temperature is preferably in the range of $-30°$ to $120°$ C., and more preferably, in the range of $0°$ to $100°$ C.

The reaction period is preferably in the range of 1 to 190 hours, and more preferably in the range of 5 to 160 hours.

The cyclopentanone carboxylate compounds of formula (IV) include two optical isomers of formulae (IVA) and (IVA') below.

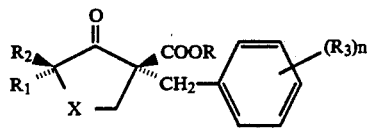

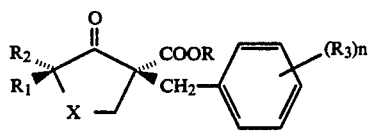

In step (b):

The cyclopentanone carboxylate compounds of formula (IV) are refluxed with inorganic acids or organic acids as mentioned above, hydrolyzed, and decarboxylated to obtain the cyclopentanone compounds of formula (III).

The reaction period is preferably in the range of 1 to 24 hours, and more preferably, in the range of 2 to 12 hours.

The cyclopentanone compounds of formula (III) include two optical isomers of formula (IIIA) and (IIIA') below.

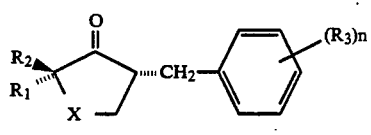

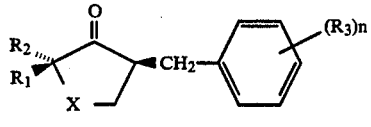

In step (c):

The cyclopentanone compounds of formula (III) are dissolved in the diluent above and reacted with sulfur ylide to obtain the oxirane compounds of formula (II).

The reaction temperature is preferably in the range of $-10°$ to $130°$ C., and more preferably, in the range of $5°$ to $100°$ C. The reaction period is preferably in the range of 0.1 to 8 hours, and more preferably in the range of 0.2 to 4 hours.

The sulfur ylide can be obtained as follows. Trimethylsulfoxonium iodide is dissolved in dimethyl sulfoxide at room temperature, and sodium hydride washed with hexane is added to the solution at room temperature to obtain sulfur ylide with evolution of hydrogen gas.

The oxirane compounds of formula (II) obtained in step (c) include four optical isomers of formulae (IIA), (IIA'), (IIB), and (IIB').

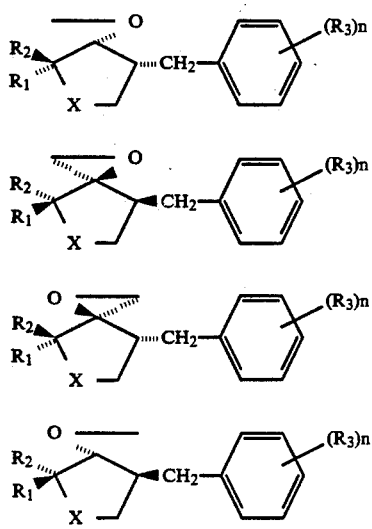

The oxirane compounds of formula (II) are reacted with solutions of sodium salts of 1H-1,2,4-triazole or sodium salts of imidazole of formula (II') in a diluent to obtain the azole compounds of formula (I).

That is, to the solutions of sodium salts of 1H-1,2,4-triazole or sodium salts of imidazole of formula (II) in a diluent, a base is added if necessary, and then oxirane compounds of formula (II) are added. Alternatively, oxirane compounds of formula (II) may be dissolved first in the diluent, followed by adding alkali metal salts of 1H-1,2,4-triazole or alkali metal salts of imidazole.

The reaction temperature is preferably in the range of 10° to 120° C., and, more preferably, in the range of 20° to 100° C.

The reaction period is in the range of 0.1 to 10 hours, preferably in the range of 0.3 to 5 hours.

The resulting solution is cooled and extracted with an organic solvent, such as ethyl acetate, chloroform, methylene chloride or benzene, while being placed in ice-cold water. The resultant layer of organic solution is collected.

The collected organic solution is washed with water, and the solvent is removed by evaporation under reduced pressure.

The obtained residue is recrystallized or chromatographed for purification to obtain the azole compounds of formula (I).

The azole compounds of formula (I) have optical isomers of formula (IA), (IA'), (IB), and (IB').

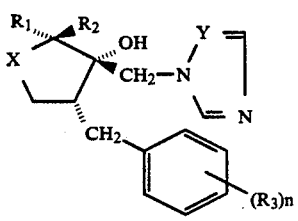

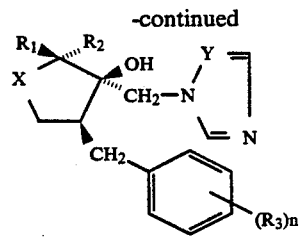

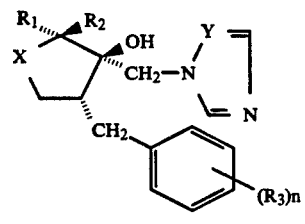

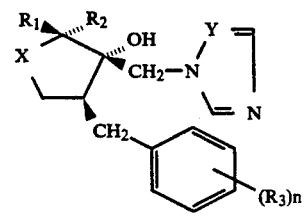

Representative azole derivatives of formula (I) of the present invention are shown in Tables 1 to 7. Each compound in Tables 1 to 7 has the structures of formulae (IA) and (IA') above, wherein: Me is methyl; Et is ethyl; iPr is isopropyl; Bu is n-butyl; t-Bu is t-butyl; and Ph is phenyl.

Novel compounds of formulae (I), (II), (III), (IV), and (V) may possibly have two or three different substituents that have replaced hydrogen atoms of the heterocyclopentane ring and, therefore, have stereoisomers. The present invention includes each of such stereoisomers and a mixture thereof.

Separation of the stereoisomers above can be carried out by means of ordinary methods such as chromatography or recrystallization.

The novel azole derivatives of formula (I) may be used in the form of pharmaceutically acceptable salts thereof.

The evaluation of antimycotic activity can be carried out by administering a dosage of the compound in the tail vein of mice that have been inoculated with a strain of Candida albicans, preferably orally, and observing the mortality of the inoculated mice for 20 days.

The survival rate was calculated from the mean survival days.

The azole derivatives of formula (I) have antimycotic activity and are useful for treating mycosis. For example, these azole derivatives are useful for treating local mycosis of humans caused by fungi of the genera such as Candida, Trichophyton, Microsporum, and Epidermophyton or mucosal mycosis caused by Candida albicans, e.g., oral- and vaginal-Candidiasis.

The azole derivatives of formula (I) can also be used for treating systemic mycosis caused by Candida albicans, Cryptococcus neoformans, Aspergillus fumigatus or fungi of the genera such as Coccidioides, Paracoccidioides, Histoplasma, and Blastomyces.

The aromatase enzyme-inhibitory activity was determined in the manner described by Covey, D.F., Biochem. Biophys. Res. Commun., 157 (1), 81–86, 1988.

More specifically, the aromatase-inhibitory activity of a compound of formula (I) was evaluated in terms of the concentration ($IC_{50}$) of the compound causing 50% inhibition of the aromatase activity.

The $IC_{50}$ values of the azole compounds (I) did not exceed $7 \times 10^{-6}$M.

Thus, the azole compounds (I) of the present invention are useful as aromatase inhibitors.

The aromatase aromatizes the A ring of steroid hormones. The proliferation of tumors, such as breast cancer, prostatic cancer, ovarian cancer, uterine tumor, pancreatic carcinoma, endometriosis, polycystic ovarian disease, benign breast disease, and Cushing's syndrome, depends upon steroid hormones having the A ring, particularly, estrogen.

Therefore, the azole derivatives of formula (I) having aromatase-inhibitory activity are useful for treating various tumors, namely the compounds of formula (I) are useful as antitumor agents.

The azole derivatives of formula (I) may be used alone. However, they are generally administered in the form of a mixture with carriers and/or diluents selected in accordance with the routes of administration and the methods of standard preparations.

The azole derivatives of formula (I) are administered in an amount of 0.001 to 300 mg/kg of patient body weight per day, orally or parenterally, and preferably, in the range of 0.01 to 100 mg/kg.

The above doses are for average cases and there exist cases which go beyond the above range. Such cases are included within the scope of this invention.

The azole derivatives of the present invention are administered to a patient from one to four times per day.

TABLE 1

| Comp. No. | $R_1$ | $R_2$ | $R_3$ | n | X | Y |
|---|---|---|---|---|---|---|
| 1 | Me | H | 4-F | 1 | O | N |
| 2 | Me | H | 4-F | 1 | O | CH |
| 3 | Me | H | 4-F | 1 | S | N |
| 4 | Me | H | 4-F | 1 | S | CH |
| 5 | Me | H | 4-F | 1 | NH | N |
| 6 | Me | H | 4-F | 1 | NH | CH |
| 7 | Me | H | 2-F | 1 | O | N |
| 8 | Me | H | 2-F | 1 | O | CH |
| 9 | Me | H | 2-F | 1 | S | N |
| 10 | Me | H | 2-F | 1 | S | CH |
| 11 | Me | H | 2-F | 1 | NH | N |
| 12 | Me | H | 2-F | 1 | NH | CH |
| 13 | Me | Me | 4-F | 1 | O | N |
| 14 | Me | Me | 4-F | 1 | O | CH |
| 15 | Me | Me | 4-F | 1 | S | N |
| 16 | Me | Me | 4-F | 1 | S | CH |
| 17 | Me | Me | 4-F | 1 | NH | N |
| 18 | Me | Me | 2-F | 1 | O | N |
| 19 | Me | Me | 2-F | 1 | S | N |
| 20 | Me | Me | 2-F | 1 | NH | N |

TABLE 2

| Comp. No. | $R_1$ | $R_2$ | $R_3$ | n | X | Y |
|---|---|---|---|---|---|---|
| 21 | H | H | 4-F | 1 | O | N |
| 22 | H | H | 4-F | 1 | O | CH |
| 23 | H | H | 2-F | 1 | O | N |
| 24 | H | H | 2-F | 1 | O | CH |
| 25 | H | H | 4-F | 1 | S | N |
| 26 | H | H | 4-F | 1 | S | CH |
| 27 | H | H | 2-F | 1 | S | CH |
| 28 | H | H | 2-F | 1 | NH | N |
| 29 | H | H | 4-Cl | 1 | O | N |
| 30 | H | H | 4-Cl | 1 | S | N |
| 31 | H | H | 2-Cl | 1 | O | CH |
| 32 | H | H | 2-Cl | 1 | S | N |
| 33 | Me | Me | 4-Cl | 1 | O | N |

TABLE 2-continued

| Comp. No. | $R_1$ | $R_2$ | $R_3$ | n | X | Y |
|---|---|---|---|---|---|---|
| 34 | Me | Me | 4-Cl | 1 | O | CH |
| 35 | Me | Me | 4-Cl | 1 | S | N |
| 36 | Me | Me | 4-Cl | 1 | S | CH |
| 37 | Me | Me | 2-Cl | 1 | O | N |
| 38 | Me | Me | 2-Cl | 1 | O | CH |
| 39 | Me | Me | 2-Cl | 1 | NH | N |
| 30 | Me | Me | 2-Cl | 1 | NH | CH |

TABLE 3

| Comp. No. | $R_1$ | $R_2$ | $R_3$ | n | X | Y |
|---|---|---|---|---|---|---|
| 41 | Me | Me | 2,4-$F_2$ | 2 | O | N |
| 42 | Me | Me | 2,4-$F_2$ | 2 | O | CH |
| 43 | Me | Me | 2,4-$F_2$ | 2 | S | N |
| 44 | Me | Me | 2,4-$F_2$ | 2 | S | CH |
| 45 | Me | Me | 2,4-$F_2$ | 2 | NH | N |
| 46 | Me | ME | 2,4-$F_2$ | 2 | NH | CH |
| 47 | Me | Me | 2,4-$Cl_2$ | 2 | O | N |
| 48 | Me | Me | 2,4-$Cl_2$ | 2 | O | CH |
| 49 | Me | Me | 2,4-$Cl_2$ | 2 | S | N |
| 50 | Me | Me | 2,4-$Cl_2$ | 2 | S | CH |
| 51 | Me | Me | 2,4-$Cl_2$ | 2 | NH | N |
| 52 | Me | Me | 2,4-$Cl_2$ | 2 | NH | CH |
| 53 | Me | Me | 4-CN | 1 | O | N |
| 54 | Me | Me | 4-CN | 1 | O | CH |
| 55 | Me | Me | 4-CN | 1 | S | N |
| 56 | Me | Me | 4-CN | 1 | S | CH |
| 57 | Me | Me | 4-CN | 1 | NH | N |
| 58 | Me | Me | 4-CN | 1 | NH | CH |
| 59 | Me | Me | 2-CN | 1 | O | N |
| 60 | Me | Me | 2-CN | 1 | S | CH |

TABLE 4

| Comp. No. | $R_1$ | $R_2$ | $R_3$ | n | X | Y |
|---|---|---|---|---|---|---|
| 61 | Me | Me | 2,4-$(CN)_2$ | 2 | O | N |
| 62 | Me | Me | 2,4-$(CN)_2$ | 2 | O | CH |
| 63 | Me | Me | 2,4-$(CN)_2$ | 2 | S | N |
| 64 | Me | Me | 2,4-$(CN)_2$ | 2 | S | CH |
| 65 | Me | Me | 2,4-$(CN)_2$ | 2 | NH | N |
| 66 | Me | Me | 2,4-$(CN)_2$ | 2 | NH | CH |
| 67 | Me | Me | 2-Ph | 1 | O | N |
| 68 | Me | Me | 2-Ph | 1 | O | CH |
| 69 | Me | Me | 2-Ph | 1 | S | N |
| 70 | Me | Me | 2-Ph | 1 | S | CH |
| 71 | Me | Me | 2-Ph | 1 | NH | N |
| 72 | Me | Me | 2-Ph | 1 | NH | CH |
| 73 | Me | Me | 4-ph | 1 | O | N |
| 74 | Me | Me | 4-Ph | 1 | O | CH |
| 75 | Me | Me | 4-Ph | 1 | S | N |
| 76 | Me | Me | 4 Ph | 1 | S | CH |
| 77 | Me | Me | 4-Ph | 1 | NH | N |
| 78 | Me | Me | 4-Ph | 1 | NH | CH |
| 79 | H | Me | 4-F | 1 | O | N |
| 80 | H | Me | 4-F | 1 | O | CH |

TABLE 5

| Comp. No. | $R_1$ | $R_2$ | $R_3$ | n | X | Y |
|---|---|---|---|---|---|---|
| 81 | H | Me | 4-F | 1 | S | N |
| 82 | H | Me | 4-F | 1 | NH | CH |
| 83 | H | Me | 2-F | 1 | O | N |
| 84 | H | Me | 2-F | 1 | S | CH |
| 85 | H | Me | 2-F | 1 | NH | N |
| 86 | Et | H | 4-F | 1 | O | N |
| 87 | Et | H | 4-F | 1 | S | N |
| 88 | Et | H | 4-F | 1 | NH | CH |
| 89 | Et | H | 2-F | 1 | O | CH |
| 90 | Et | H | 2-F | 1 | S | N |
| 91 | Et | H | 2-F | 1 | NH | CH |
| 92 | H | Et | 4-F | 1 | O | CH |
| 93 | H | Et | 4-F | 1 | S | N |
| 94 | H | Et | 2-F | 1 | NH | N |
| 95 | H | Et | 2-F | 1 | NH | CH |
| 96 | Pr | H | 4-F | 1 | O | N |
| 97 | iPr | H | 4-F | 1 | O | CH |

TABLE 5-continued

| Comp. No. | $R_1$ | $R_2$ | $R_3$ | n | X | Y |
|---|---|---|---|---|---|---|
| 98 | Pr | H | 4-F | 1 | S | N |
| 99 | Pr | H | 2-F | 1 | O | N |
| 100 | Pr | H | 2-F | 1 | S | CH |

TABLE 6

| Comp. No. | $R_1$ | $R_2$ | $R_3$ | n | X | Y |
|---|---|---|---|---|---|---|
| 101 | Pr | H | 2-F | 1 | NH | N |
| 102 | iPr | H | 2,4-$F_2$ | 2 | O | N |
| 103 | Pr | H | 2,4-$F_2$ | 2 | S | CH |
| 104 | Pr | H | 2,4-$F_2$ | 2 | NH | N |
| 105 | H | Pr | 4-F | 1 | O | CH |
| 106 | H | Pr | 4-F | 1 | S | N |
| 107 | H | iPr | 4-F | 1 | NH | CH |
| 108 | H | Pr | 2-F | 1 | O | CH |
| 109 | H | iPr | 2-F | 1 | S | N |
| 110 | H | Pr | 2,4-$F_2$ | 2 | O | CH |
| 111 | H | iPr | 2,4-$F_2$ | 2 | S | N |
| 112 | H | Pr | 2,4-$F_2$ | 2 | NH | CH |
| 113 | Bu | H | 4-F | 1 | O | N |
| 114 | Bu | H | 4-F | 1 | S | CH |
| 115 | Bu | H | 4-F | 1 | NH | N |
| 116 | tBu | H | 2-F | 1 | O | N |
| 112 | Bu | H | 2-F | 1 | S | CH |
| 118 | tBu | H | 2-F | 1 | NH | N |
| 119 | Bu | H | 2,4-$F_2$ | 2 | O | N |
| 120 | Bu | H | 2,4-$F_2$ | 2 | S | CH |

TABLE 7

| Comp. No. | $R_1$ | $R_2$ | $R_3$ | n | X | Y |
|---|---|---|---|---|---|---|
| 121 | Bu | H | 2,4-$F_2$ | 2 | NH | N |
| 122 | H | Bu | 4-F | 1 | O | N |
| 123 | H | tBu | 4-F | 1 | O | CH |
| 124 | H | Bu | 4-F | 1 | S | N |
| 125 | H | tBu | 4-F | 1 | NH | N |
| 126 | H | Bu | 2-F | 1 | O | N |
| 127 | H | Bu | 2-F | 1 | S | CH |
| 128 | H | tBu | 2-F | 1 | NH | N |
| 129 | H | Bu | 2,4-$F_2$ | 2 | O | CH |
| 130 | H | tBu | 2,4-$F_2$ | 2 | O | N |
| 131 | H | Bu | 2,4-$F_2$ | 2 | S | CH |
| 132 | H | Bu | 2,4-$F_2$ | 2 | NH | N |
| 133 | H | Bu | 2,4-$Cl_2$ | 2 | O | N |
| 134 | H | Bu | 2,4-$Cl_2$ | 2 | S | CH |
| 135 | H | Bu | 2,4-$Cl_2$ | 2 | NH | CH |
| 136 | H | tBu | 4-Cl | 1 | O | N |
| 137 | H | Bu | 4-Cl | 1 | S | CH |
| 138 | H | Bu | 2-Cl | 1 | O | N |

EXAMPLES

The present invention is illustrated by specific examples. However, this is not intended to limit the scope of the present invention in any way. In the following examples, elemental analysis was carried out by detecting the decomposed gas of the compounds with a TCD detector in an automatic elemental analyzer (MT3; manufactured by YANAGIMOTO SEISAKUSHO).

The optical rotation $[\alpha]_D$ was determined with an automatic spectropolarimeter (DIP-360; manufactured by NIHON BUNKO CO.).

The NMR spectra were recorded in ppm on a JNM-GSX 500 spectrometer (manufactured by NIHON DENSHI CO.) in $CDCl_3$ relative to $Me_4Si$.

The IR spectrum was measured with a spectrophotometer (A-202; manufactured by NIHON BUNKO CO.) using a KBr or neat method and $V_{max}$ was determined.

Thin layer chromatography was performed with n-hexane-ethyl acetate or ethyl acetate to measure Rf.

Further, mp was measured with a micro melting point detector (manufactured by YANAGIMOTO SEISAKUSHO).

EXAMPLE 1

[1] Synthesis of 4-carbomethoxy-4-(4-fluorobenzyl)-2-methyl-tetrahydrofuran-3-one (4-1)

Sodium hydride (0.25 g, 10.5 mmol) was suspended in freshly distilled tetrahydrofuran (10 ml) and the suspension was stirred on a water bath. A solution of 4-carbomethoxy-2-methyltetrahydrofuran-3-one (5-1) (1.58 g, 10 mmol) in distilled tetrahydrofuran (10 ml) was added dropwise to the suspension and stirred for 30 min. 4-Fluorobenzylbromide (2.08 g, 11.0 mmol) was added dropwise to the suspension and stirred overnight.

At the end of the reaction, which had been confirmed by thin layer chromatography, the resulting solution was poured into ice-cold water and extracted with diethyl ether.

The organic layer was washed with brine and dried over anhydrous sodium sulfate. The dried solution was concentrated under reduced pressure to obtain a crude product (2.87 g). The crude product was chromatographed on a silica gel column with n-hexane-ethyl acetate (4:1) to obtain the title compound as a colorless liquid (4-1) (2.13 g, 80.4%).

The physicochemical properties of the liquid are as follows:

Rf: 0.46 (n-hexane-ethyl acetate=2:1). IR($V_{max}$, $cm^{-1}$, neat): 3000m, 2960m, 2895m, 1765s, 1735s, 1601s, 1520s, 1440s, 1370m, 1261s, 1220s.

$^1$H-NMR ($\delta$ppm, $CDCl_3$): 1.55 (d, 3H), 1.32 (d, 3H), 3.06 (d, 1H), 3.12 (d, 1H), 3.22 (d, 1H), 3.25 (d, 1H), 3.67 (q, 1H), 3.91 (d, 1H), 4.00 (q, 1H), 4.19 (d, 1H), 4.40 (d, 1H), 4.58 (d, 1H), 6.97 (m, 4H), 7.11 (M, 4H).

[2] Synthesis of 4-(4-fluorobenzyl)-2-methyltetrahydrofuran-3-one (3-1)

Glacial acetic acid (11 ml) and an aqueous solution of sulfuric acid (12.5%, 5 ml) were added to 4-carbomethoxy-4-(4-fluorobenzyl)-2-methyltetrahydrofuran-3-one (4-1) (1.51 g, 5.6 mmol), and the mixture was refluxed for 4 hours under argon.

At the completion of the reaction, which had been confirmed by thin layer chromatography, the resulting solution was poured into ice-cold water and extracted with diethyl ether.

The organic layer was washed with brine, dried over anhydrous sodium sulfate, and concentrated under reduced pressure to obtain a crude product (1.55 g). The crude product was purified by silica gel column chromatography using n-hexane-ethyl acetate (2:1) to obtain the title compound as a yellow liquid (3-1) (0.97 g, 80.8%).

Rf: 0.55 (n-hexane-ethyl acetate=2:1).

IR ($V_{max}$, $cm^{-1}$, neat): 2975w, 2930w, 2855w, 1758s, 1601w, 1515s, 1220s.

$^1$H-NMR ($\delta$ppm, $CDCl_3$): 1.22 (d, 3H), 1.32 (d, 3H), 2.63 (d, 1H), 2.66 (d, 1H), 2.76 (m, 2H), 3.01 (d, 0.5H), 3.03 (d, 0.5H), 3.10 (d, 0.5H), 3.13 (d, 0.5H), 3.67 (t, 1H), 4.31 (t, 1H), 6.97 (m, 4H), 7.11 (m, 4H)

[3] Synthesis of 7-(4-fluorobenzyl)-2-methyl-1,5-dioxaspiro [2.4] heptane (2-1)

Trimethylsulfoxonium iodide (0.57 g, 2.2 mmol) was dissolved in dimethyl sulfoxide (4 ml), and sodium hydride (0.06 g, 2.4 mmol) was added to the solution being stirred at 10° C. The solution was warmed to room temperature, stirred for 30 minutes, after which the solution was cooled to 10° C. 4-(4-Fluorobenzyl)-2-methyl-tetrahydrofuran-3-one (3-1) (0.42 g, 2.0 mmol) was added to the solution dropwise, which was then warmed to room temperature, and stirred for 30 minutes.

At the end of the reaction, which had been confirmed by thin layer chromatography, the resulting solution was added into ice-cold water and extracted with diethyl ether.

The organic layer was washed with brine and dried over anhydrous sodium sulfate.

The dried solution was concentrated under reduced pressure to obtain a crude product as a yellow liquid having the structures of formulae (IIA) and (IIA') above (2-1) (0.32 g, 72.7%).

Rf: 0.33 (n-hexane-ethyl:acetate=2:1)

[4] Synthesis of 4-(4-fluorobenzyl)-3-hydroxy-2-methyl-3-(1H-1,2,4-triazol-1-ylmethyl) tetrahydrofuran (Compound No. 1)

7-(4-Fluorobenzyl)-2-methyl-1,5-dioxaspiro [2.4] tetrahydrofuran (2-1) having the structures of formulae (IIA) and (IIA') obtained from Example 1 [3] (532.3 mg, 2.39 mmol) was dissolved in dimethylformamide (3.0 ml). Sodium salt of 1H-1,2,4-triazole (283.5 mg, 3.11 mmol) was added to the solution, which was then stirred at 70° C. for 1 hour in an atmosphere of argon.

At the end of the reaction, which had been confirmed by thin layer chromatography, the reaction mixture was poured into ice-cold water (10 ml) and extracted with ethyl acetate (50 ml×2).

The ethyl acetate layers were dried over anhydrous sodium sulfate and concentrated under reduced pressure to obtain a crude product (875.5 mg).

The crude product was chromatographed on a silica gel (dia. 2.5 cm×height 10 cm, 15 g) with ethyl acetate to obtain the title product as white crystals having the structures of general formulae (IA) and (IA') described above (Comp. No. 1) (489.8 mg, 69.9%).

Rf: 0.28 (ethyl acetate) mp: 106°–108° C.

IR ($V_{max}$, cm$^{-1}$, KBr): 3200s, 3160s, 2991s, 2950s, 2880m, 1600m, 1519s, 1440m, 1420m, 1382m, 1275s, 1219s, 1200s, 1159s, 1119s, 1030s, 965m, 750s, 680s.

$^1$H-NMR (δppm, CDCl$_3$): 0.91 (d, 3H), 2.3–2.6 (m, 3H), 3.65 (t, 1H), 3.79 (t 1H), 3.8–3.9 (m, 1H), 4.16 (d, 1H), 4.20 (d, 1H), 6.97 (m, 2H), 7.10 (m, 2H), 7.97 (2, 1H), 8.09 (s, 1H).

[5] Synthesis of 4-(4-fluorobenzyl)-3-hydroxy-3-(imidazol-1-ylmethyl)-2-methyl tetrahydrofuran (Comp. No. 2)

7-(4-Fluorobenzyl)-2-methyl-1,5-dioxaspiro[2.4] heptane having the structures of general formulae (IIA) and (IIA') (2-1) (0.32 g, 1.4 mmol) was dissolved in dimethylformamide (3.0 ml). Sodium salt of imidazole (0.17 g, 1.9 mmol) was added to the solution, which was then stirred at 70° C. in an atmosphere of argon for 1 hour. At the end of the reaction, which had been confirmed by thin layer chromatography, the resulting solution was added to ice-cold water and extracted with ethyl acetate. The organic layer was washed with brine, dried over anhydrous sodium sulfate, and concentrated under reduced pressure to obtain a crude product as white crystals having the structures of general formulae above (IA) and (IA') (Comp. No. 2) (0.56 g).

mp: 114°–118° C.

IR ($V_{max}$, cm$^{-1}$, KBr): 3400s, 3100s, 2980s, 2940s, 2860m, 1515s, 1435m, 1270m, 1210s, 1107s, 1075s, 1022s, 820s, 760s, 665s, $^1$H-NMR (δppm, CDCl$_3$): 0.95 (d, 3H), 2.4–2.5 (m, 3H), 3.64 (t, 1H), 3.80 (t, 1H), 3.92 (d, 1H), 3.96 (d, 1H), 6.96 (m, 3H), 7.07 (m, 3H), 7.51 (s, 1H).

EXAMPLE 2

[1] Synthesis of 4-carbomethoxy-2,2-dimethyltetrahydrofuran-3-one (5-13)

n-Hexane-washed sodium hydride (1.2 g, 50 mmol) and ether (30 ml) were placed in a 200 ml round-bottomed flask. Methyl α-hydroxy-isobutyrate (5.95 g, 50 mmol) was slowly dripped into the suspension at 0° C. Hydrogen gas was vigorously generated by exothermic reaction. The resulting solution was stirred at room temperature for 10 minutes, followed by removing ether under reduced pressure with an evaporator. Dimethyl sulfoxide (20 ml) was added to the dried residue immediately followed by adding methyl acrylate (4.73 g, 55 mmol) all at once.

As a result, the suspension gradually turned to light yellow.

The resulting solution was stirred at room temperature for 15 minutes and then the reaction was stopped with a 5 N-HCl aqueous solution (100 ml).

The reaction mixture was extracted with ether (100 ml×2). The ether layers were washed with distilled water and dried over anhydrous sodium sulfate. The solvent was removed by evaporation using an evaporator to obtain a light yellow oil (8.09 g), followed by vacuum distillation (5 mm Hg) to obtain the title compound as a colorless oil (5-13) (4.77 g, 55.5%).

Rf: 0.48 (n-hexane-ethyl acetate=2:1) bp: 61°–63° C./5 mm Hg.

IR ($V_{max}$, cm$^{-1}$, neat): 3000m, 2950m, 1770s, 1735s, 1420m, 1322m, 1170m .

$^1$H-NMR (δppm, CDCl$_3$): 1.28 (s, 3H), 1.29 (s, 3H), 3.58 (t, 1H), 3.78 (s, 3H), 4.39 (d, 1H), 4.73 (d, 1H)

[2] Synthesis of 4-carbomethoxy-4-(4-fluorobenzyl)-2,2-dimethyl-tetrahydrofuran-3-one (4-13)

n-Hexane-washed sodium hydride (114.0 mg, 6.0 mmol) was suspended in freshly distilled tetrahydrofuran (10 ml), and 4-carbomethoxy-2, 2-dimethyltetrahydrofuran-3-one (5-13) (861.0 mg, 10.0 mmol) was dripped into the suspension at 0° C. over a period of at least 5 minutes.

The reaction was exothermic and hydrogen gas was generated. In about 2 minutes, the reaction mixture turned to a light yellow solution. After the solution had been stirred for about 30 minutes, 4-fluorobenzylbromide (1.98 g. 10.5 mmol) was added to the solution at 0° C. The solution was stirred for 72 hours at 25° C., followed by adding distilled water (20 ml) and extracting the solution with ether (50 ml×2). The ether layers were washed with brine and with distilled water, and then dried over anhydrous sodium sulfate. The solvent was removed by using an evaporator to obtain a crude product (2.89 g).

The crude product was chromatographed on a silica gel column (dia. 2.5 cm×height 8.0 cm, 10 g) with n-hexane-ethyl acetate (4:1) to obtain the title product as a colorless liquid (4-13) (1.33 g, 94.7%).

Rf: 0.54 (n-hexane-ethyl acetate=2.1)

IR ($V_{max}$, cm$^{-1}$, neat): 3000m, 2975m, 2900m, 1770s, 1730s, 1610m, 1520s.

$^1$H-NMR ($\delta$ppm, CDCl$_3$): 0.96 (s, 3H), 1.28 (s, 3H), 3.12 (d, 1H), 3.22 (d, 1H), 3.75 (s, 3H), 4.02 (d, 1H), 4.49 (d, 1H), 6.96 (t, 2H), 7.12 (m, 2H).

[3] Synthesis of 4-(4-fluorobenzyl)-2,2-dimethyltetrahydrofuran-3-one (3-13)

Glacial acetic acid (9 ml) and an aqueous solution of sulfuric acid (12.5%, 5 ml) were added to 4-carbomethoxy-4-(4-fluorobenzyl)-2,2-dimethyltetrahydrofuran-3-one (4-13) (1.32 g, 4.7 mmol). The mixture was refluxed in an atmosphere of argon for 4 hours.

At the end of the reaction, which had been confirmed by thin layer chromatography, the resulting solution was poured into ice-cold water and extracted with diethyl ether.

The organic layers were washed with brine, dried over anhydrous sodium sulfate, and concentrated under reduced pressure to obtain a crude product (1.32 g). The crude product was chromatographed on a silica gel column with n-hexane-ethyl acetate (2:1) to obtain the title product as a yellow liquid (3-13) (0.99 g, 94.7%).

Rf: 0.52 (n-hexane-ethyl acetate=2:1)

IR ($V_{max}$, cm$^{-1}$, neat): 3010m, 2960m, 2900m, 1762s, 1610m, 1522s.

$^1$H-NMR ($\delta$ppm, CDCl$_3$): 1.10 (s, 3H), 1.27 (s, 3H), 2.69 (dd, 1H), 2.81 (m, 1H), 3.08 (dd, 1H), 3.77 (t, 1H), 4.19 (t, 1H), 6.97 (t, 2H), 7.11 (t, 2H)

[4] Synthesis of 7-(4-fluorobenzyl)-4,4-dimethyl-1,5-dioxaspiro[2.4]heptane (2-13)

Trimethylsulfoxonium iodide (0.22 g, 1.3 mmol) was dissolved in dimethyl sulfoxide (2 ml) at room temperature. While stirring the solution at 10° C., sodium hydride (0.03 g, 1.2 mmol) was added.

The solution was warmed to room temperature, stirred for 40 minutes, and again cooled to 10° C. While stirring the solution, 4-(4-fluorobenzyl)-2,2-dimethyltetrahydrofuran-3-one (3-13) (0.22 g, 1.0 mmol) was added. The solution was stirred for 10 minutes, warmed to room temperature, and again stirred for 35 minutes. Ice-cold water was then added to cease the reaction.

The resulting solution was extracted with diethyl ether. The organic layer was washed with brine, and dried over anhydrous sodium sulfate.

The dried solution was concentrated under reduced pressure to obtain a crude product as a light yellow liquid (2-13) having the structures of general formulae (IIA) and (IIA') above (0.19 g, 82.6%).

Rf: 0.49 (n-hexane-ethyl acetate=2:1).

[5] Synthesis of 4-(4-fluorobenzyl)-3-hydroxy-2,2-dimethyl-3(1H-1,2,4-triazole-1-ylmethyl) tetrahydrofuran (Compound No. 13)

7-(4-Fluorobenzyl)-4,4-dimethyl-1,5-dioxaspiro[2.4]heptane (2-13) having the structures of general formulae (IIA) and (IIA') above (106.2 mg, 0.45 mmol) was dissolved in dimethylformamide (3 ml). Sodium salt of 1H-1,2,4-triazole (53.2 mg, 0.58 mmol) was added to the solution at room temperature, and the solution was then stirred at 70° C. in an atmosphere of argon for 1 hour.

At the end of the reaction, the resulting solution was poured into ice-cold water (5 ml) and extracted with diethyl ether (30 ml×2).

The organic layers were washed with brine, dried over anhydrous sodium sulfate, and concentrated under reduced pressure to obtain a crude product (103.3 mg).

The crude product was chromatographed on a silica gel column (dia. 2.5 cm×height 2.8 cm, 3.9 g) with ethyl acetate to obtain the title product as white crystals having the structures of general formulae (IA) and (IA') above (Compound No. 13) (68.4 mg, 49.5%).

Rf: 0.28 (ethyl acetate). mp: 123°-124° C.

IR ($V_{max}$, cm$^{-1}$, KBr): 3400m, 3220m, 3160m, 2950s, 1601s, 1519s, 1219.

$^1$H-NMR ($\delta$ppm, CDCl$_3$): 0.89 (s, 3H), 1.28 (s, 3H), 2.47 (m, 1H), 2.60 (m, 2H), 3.63 (t, 1H), 3.86 (t, 1H), 4.21 (q, 2H), 6.95 (m, 2H), 7.05 (m, 2H), 7.96 (s, 1H), 8.22 (s, 1H).

[6] Synthesis of 4-(4-fluorobenzyl)-3-hydroxy-3-(imidazol-1-ylmethyl)-2,2-dimethyltetrahydrofuran (Compound No. 14)

4,4-Dimethyl-7-(4-fluorobenzyl)-1,5-dioxaspiro[2.4]heptane (2-13) having the structures of general formulae (IIA) and (IIA') above (0.20 g, 0.8 mmol) was dissolved in dimethylformamide (3 ml). Sodium salt of imidazole (0.10 g, 1.1 mmol) was added to the solution, which was then stirred at 70° C. in an atmosphere of argon for 1 hour.

At the end of the reaction, which had been confirmed by thin layer chromatography, the resulting solution was poured into ice-cold water and extracted with ethyl acetate.

The organic layer was washed with brine, dried over anhydrous sodium sulfate, and concentrated under reduced pressure to obtain a crude product (0.28 g). The crude product was chromatographed on a silica gel column with ethyl acetate. The obtained fraction was further recrystallized from n-hexane-ethyl acetate to obtain the title product as white crystals having the structures of general formulae (IA) and (IA') above (Compound No. 14) (0.11 g, 42.3%).

Rf: 0.08 (ethyl acetate) mp: 159°-162° C.

IR ($V_{max}$, cm$^{-1}$, KBr): 3430m, 3125m, 3000m, 2900m, 2850m, 1601w, 1518s.

$^1$H-NMR ($\delta$ppm, CDCl$_3$): 0.95 (s, 3H), 1.27 (s, 3H), 2.37 (dd, 1H), 2.54 (dd, 1H), 2.61 (m, 1H), 3.60 (t, 1H), 3.86 (t, 1H), 3.94 (d, 1H), 4.00 (d, 1H), 6.96 (m, 2H), 7.06 (m, 4H), 7.61 (s, 1H).

EXAMPLE 3

[1] Synthesis of 4-carbomethoxy-4-(4-chlorobenzyl)-2,2-dimethyltetrahydrofuran-3-one (4-33)

n-Hexane-washed sodium hydride (240.0 mg, 10.0 mmol) and tetrahydrofuran (10 ml) were placed in an eggplant, shaped flask (50 ml). 4-Carbomethoxy-2,2-dimethyltetrahydrofuran-3-one (1.72 g, 10.0 mmol) was slowly dripped into the suspension at 0° C. over a period of at least 5 minutes.

Hydrogen gas was soon generated and the reaction mixture turned to a light yellow solution. The resulting solution was stirred at 0° C. for 10 minutes and then 4-chlorobenzyl chloride (1.69 g, 10.5 mmol) was slowly dripped thereto at 0° C.

The resulting solution was stirred at room temperature for 3 days and then further stirred at 60° C. for 3 days, which was required because of the slow reaction. At the end of the reaction, distilled water was added to the resulting solution, which was then extracted with ether (100 ml×2). The ether layers were washed with brine, dried over anhydrous sodium sulfate, and the solvent was removed by evaporation under reduced pressure to obtain a crude product (3.31 g). The resulting crude product was chromatographed on a silica gel column (dia. 2.5 cm×height 14 cm, 20 g) with n-hexane-ethyl acetate (4:1) to obtain the title product as a yellow liquid above (4–33) (2.43 g, 81.8%).

Rf: 0.40 (n-hexane-ethyl acetate=2:1)

IR ($V_{max}$, cm$^{-1}$, neat): 3650w, 3500w, 2975m, 2950m, 1765s, 1730s, 1595m, 1495s, 1435m, 1408m, 1377m, 1360m, 1220s, 1090s, 1012s.

$^1$H-NMR (δppm, CDCl$_3$): 0.99 (s, 3H), 1.28 (s, 3H), 3.10 (d, 1H), 3.23 (d, 1H), 3.75 (s, 3H), 4.01 (d, 1H), 4.49 (d, 1H), 7.08 (d, 2H), 7.25 (d, 2H).

[2] Synthesis of 4-(4-chlorobenzyl)-2,2-dimethyltetrahydrofuran-3-one (3–33)

Glacial acetic acid (8 ml) and an aqueous solution of sulfuric acid (12.5%, 4 ml) were added to 4-carbomethoxy-4-(4-chlorobenzyl)-2,2-dimethyltetrahydrofuran-3-one (4–33) (0.95 g, 3.2 mmol), and the solution was refluxed for 4 hours in an atmosphere of argon.

At the end of the reaction, which had been confirmed by thin layer chromatography, the resulting solution was poured into ice-cold water and extracted with ethyl acetate (50 ml×2).

The organic layers were washed with brine and dried over anhydrous sodium sulfate. The dried solution was concentrated under reduced pressure to obtain a crude product (0.86 g). The crude product was separated by silica gel column chromatography using n-hexane-ethyl acetate (2:1) to obtain the title product as a yellow liquid (3–33) (0.71 g, 94.0%).

Rf: 0.46 (n-hexane-ethyl acetate=2:1).

IR ($V_{max}$, cm$^{-1}$, neat): 2990m, 2948m, 2890m, 1758s, 1600w, 1500s.

$^1$H-NMR (δppm, CDCl$_3$): 1.12 (s, 3H), 1.27 (s, 3H), 2.68 (dd, 1H), 2.83 (m, 1H), 3.08 (dd, 1H), 3.75 (t, 1H), 4.19 (t, 1H), 7.09 (d, 2H), 7.26 (d, 2H)

[3] Synthesis of 7-(4-chlorobenzyl)-4,4-dimethyl-1,5-dioxaspiro[2.4]heptane (2–33)

Trimethylsulfoxonium iodide (0.29 g, 1.3 mmol) was dissolved in DMSO (2 ml). While stirring the solution at 10° C., sodium hydride (0.03 g, 1.2 mmol) was added. The solution was warmed to room temperature, stirred for 30 minutes, and then again cooled to 10° C.

4-(4-Chlorobenzyl)-2,2-dimethyltetrahydrofuran-3-one (3–33) (0.24 g, 1.0 mmol) was added dropwise to the solution, which was then stirred at room temperature for 30 minutes.

At the end of the reaction, which had been confirmed by thin layer chromatography, the resulting solution was poured into ice-cold water (10 ml) and extracted with ethyl acetate (30 ml×2).

The organic layers were washed with brine, dried over anhydrous sodium sulfate, and concentrated under reduced pressure to obtain a crude product as a yellow liquid having the structures of general formulae (IIA) and (IIA') above (2–33) (0.25 g, 96.0%).

Rf: 0.48 (n-hexane-ethyl acetate=2.1).

[4] Synthesis of 4-(4-chlorobenzyl)-3-hydroxy-2,2-dimethyl-3-(1H-1,2,4-triazol-1-ylmethyl) tetrahydrofuran (Compound No. 33)

7-(4-Chlorobenzyl)-4-dimethyl-1,5-dioxaspiro[2.4]heptane (2–33) having the structures of formulae (IIA) and (IIA') above (0.25 g, 1.0 mmol) was dissolved in dimethylformamide (3 ml). Sodium salt of 1H-1,2,4-triazole (0.11 g, 1.3 mmol) was added to the solution, which was then stirred at 70° C. in an atmosphere of argon for 1 hour.

At the end of the reaction, which had been confirmed by thin layer chromatography, the resulting solution was poured into ice-cold water (10 ml) and extracted with ethyl acetate (30 ml×2).

The organic layers were washed with brine, dried over anhydrous sodium sulfate, and concentrated under reduced pressure to obtain a crude product (0.23 g).

The crude product was chromatographed on a silica gel column with ethyl acetate, and then the obtained fraction was recrystallized from n-hexane-ethyl acetate to obtain the title product as white crystals having the structures of general formulae (IA) and (IA') above (Compound No. 33) (0.06 g, 20%).

Rf: 0.18 (ethyl acetate) mp: 119°–120° C.

IR ($V_{max}$, cm$^{-1}$, KBr): 3175s, 2998m, 2950m, 2870m, 1518s, 1498s.

$^1$H-NMR (δppm, CDCl$_3$): 0.89 (s, 3H), 1.28 (s, 3H), 2.48 (m, 1H), 2.61 (m, 2H), 3.62 (d, 1H), 3.86 (d, 1H), 4.20 (d, 1H), 4.24 (d, 1H), 7.05 (m, 2H), 7.24 (m, 2H), 7.96 (s, 1H), 8.21 (s, 1H).

[5] Synthesis of 4-(4-chlorobenzyl)-3-hydroxy-3-(1H-imidazol-1-ylmethyl)-2,2-dimethyltetrahydrofuran (Compound No. 34)

7-(4-Chlorobenzyl)-4,4-dimethyl-1,5-dioxaspiro[2.4]heptane (2–33) having the stereospecific structures of general formulae (IIA) and (IIA') above (0.16 g, 0.6 mmol) was added to dimethylformamide (3 ml). Sodium salt of imidazole (0.07 g, 0.8 mmol) was added to the solution, which was then stirred at 70° C. in an atmosphere of argon for 1 hour.

At the end of the reaction, which had been confirmed by thin layer chromatography, the resulting solution was poured into ice-cold water (10 ml) and extracted with ethyl acetate (30 ml×2). The organic layers were washed with brine, dried over anhydrous sodium sulfate, and concentrated under reduced pressure to obtain a crude product (0.21 g).

The crude product was purified by silica gel column chromatography using ethyl acetate. The product was recrystallized from n-hexane-ethyl acetate to obtain the title product having the structures of formulae (IA) and (IA') above as white crystals (Compound No. 34) (0.1 g, 46.2%).

Rf: 0.04 (ethyl acetate) mp: 145°–146° C.

IR ($V_{max}$, cm$^{-1}$, KBr): 3425m, 3100m, 2975m, 2925m, 2870m, 1618w, 1510w, 1490s $^1$H-NMR (δppm, CDCl$_3$): 0.95 (s, 3H), 1.26 (s, 3H), 2.35 (dd, 1H), 2.53 (dd, 1H), 2.62 (m, 1H), 3.59 (t, 1H), 3.86 (t, 1H), 3.96 (d, 1H), 4.02 (d, 1H), 7.02 (d, 2H), 7.07 (d, 2H), 7.25 (d, 2H), 7.67 (s, 1H).

EXAMPLE 4

[1] Synthesis of 4-carbomethoxy-4-(4-cyanobenzyl)-2,2-dimethyltetrahydrofuran-3-one (4–53)

n-Hexane-washed sodium hydride (120 mg, 5.0 mmol) and tetrahydrofuran (5.0 ml) were placed in an eggplant-shaped flask (50 ml), and then 2,2-dimethyl-4-carbomethoxy-tetrahydrofuran-3- one (5–53) (860.7 mg, 5.0 mmol) was dropwise added to the suspension at 0° C. In about 2 minutes, the suspension turned into a light yellow solution. After the solution had been stirred for 20 minutes, α-bromo-p-tolunitrile (1.03 g, 5.25 mmol) was slowly dripped into the resulting solution at 0° C., followed by stirring over night at room temperature.

Distilled water (20 ml) was added to the resulting solution, which was then extracted with ether (50 ml×1, 40 ml×1).

The ether layers were washed with brine (20 ml×1) and dried over anhydrous sodium sulfate. The solvent was removed from the dried solution by using an evaporator to obtain a crude product (1.543 g). The crude product was chromatographed on a silica gel column (dia. 2.5 cm× height 14 cm) 15 g) with n-hexane-ethyl acetate (4:1) to obtain the title product as colorless crystals (4–53) (1.324 g, 92.2%).

Rf: 0.423 (n-hexane-ethyl acetate=2:1) mp: 65°–65.5° C.

IR ($V_{max}$, cm$^{-1}$, KBr): 2225 (CN), 1775 (CO), 1735 (COOCH$_3$), 1610m, 1435m, 1219s, 980s, 561s.

$^1$H-NMR (δppm, CDCl$_3$): 1.00 (s, 3H), 1.29 (s, 3H), 3.17 (d, 1H), 3.31 (d, 1H), 3.76 (s, 3H), 3.98 (d, 1H), 4.50 (d, 1H), 7.28 (d, 2H), 7.58 (d, 2H).

[2] Synthesis of 4-(4-cyanobenzyl)-2,2-dimethyltetrahydrofuran-3-one (3–53)

2,2-Dimethyl-4-carbomethoxy-4-(4-cyanobenzyl)-tetrahydrofuran-3-one (4–53) (305.6 mg, 1 mmol) and glacial acetic acid (2 ml) were placed in an eggplant-shaped flask (25 ml). An aqueous solution of sulfuric acid (1.0 ml, 12.5%) was added to the solution, which was then heated and maintained at 120° C. for 4.5 hours in an atmosphere of argon.

At the end of the reaction, which had been confirmed by thin layer chromatography, the resulting solution was poured into ice-cold water (30 ml) and extracted with diethyl ether (50 ml×1, 40 ml×1).

The ether layers were washed with brine and dried over anhydrous sodium sulfate.

The dried solution was concentrated under reduced pressure by using a rotary evaporator to obtain a crude product (298.3 mg). The crude product was chromatographed on a silica gel column (dia. 2.5 cm×height 7.0 cm, 10 g) with n-hexane-ethyl acetate (2:1) to obtain the title compound in the form of oil (3–53) (209.3 mg, 86.3%).

$^1$H-NMR (δppm, CDCl$_3$): 1.13 (s, 3H), 1.28 (s, 3H), 2.77 (dd, 1H), 2.86 (m, 1H), 3.17 (dd, 1H), 3.75 (dd, 1H), 4.22 (dd, 1H), 7.29 (d, 2H), 7.59 (d, 2H)

IR ($V_{max}$, cm$^{-1}$, neat): 2225m (CN), 1765s (CO), 1605m, 1510m, 1180m

Rf: 0.40 (n-hexane-ethyl acetate=2:1).

[3] Synthesis of 7-(4-cyanobenzyl)-4,4-dimethyl-1,5-dioxaspiro[2.4]heptane (2–53)

Trimethylsulfonium iodide (180.4 mg, 0.842 mmol) and dimethyl sulfoxide (2.0 ml) were placed in an eggplant-shaped flask (25 ml). The solution was stirred at 10° C., and n-hexane-washed sodium hydride (18.9 mg, 0.785 mmol) was added thereto. The resulting solution was stirred at room temperature for 30 minutes to obtain a transparent solution. 4-(4-Cyanobenzyl) -2,2-dimethyltetrahydrofuran-3-one (3–53) (155.9 mg, 0.683 mmol) and dimethyl sulfoxide (1.0 ml) were dissolved into the transparent solution at 10° C. The solution was stirred at room temperature for 1 hour. Distilled water was added to the solution to cease the reaction.

The resulting solution was extracted with ether. The ether layer was washed with brine, and dried over anhydrous sodium sulfate.

The dried solution was concentrated under reduced pressure to obtain a crude product having the structures of formulae (IIA) and (IIA') above (2–53) (121.6 mg).

Rf=0.40 (n-hexane-ethyl acetate=2:1).

[4] Synthesis of 2,2-dimethyl-3-(1H-1,2,4-triazol-1-ylmethyl)-3-hydroxy-5-(4-cyanobenzyl)-tetrahydrofuran (Compound No. 53)

The epoxide compound (2–53) (121.6 mg, 0.683 mmol) obtained in step [3] above was dissolved in dimethylformamide (3.0 ml), and the sodium salt of 1H-1,2,4-triazole (80.8 mg, 0.888 mmol) was added at room temperature. The mixture was reacted at 70° C. for 1.5 hours in an atmosphere of argon. At the end of the reaction, which had been confirmed by thin layer chromatography, the resulting solution was poured into ice-cold water (5 ml) and extracted with diethyl ether (50 ml×1, 30 ml×2).

The organic layers were washed with brine and dried over anhydrous sodium sulfate. The solvent was removed by using a rotary evaporator to obtain a crude product (84.3 mg), which was purified by silica gel column chromatography (dia. 1.5 cm×height 4.0 cm, 3 g) using ethyl acetate to obtain the title compound (Compound No. 53) (37.2 mg, 17.4%).

mp: 125°–127° C.

$^1$H-NMR (δppm, CDCl$_3$): 1.04 (s, 3H), 1.28 (s, 3H), 2.48 (m, 1H), 2.60 (m, 1H), 2.64 (m, 1H), 3.16 (t, 1H), 3.84 (t, 1H), 4.23 (d, 1H), 4.27 (d, 1H), 7.23 (d, 2H), 7.56 (d, 2H), 7.97 (s, 1H), 8.23 (s, 1H).

[5] Synthesis of 2,2-dimethyl-3-(imidazol-1-ylmethyl)-3-hydroxy-5-(4-cyanobenzyl)-tetrahydrofuran (Compound No. 54).

The epoxide compound obtained in Example 4[3] above (2–53) (290 mg, 1.2 mmol), dimethylformamide (2.0 ml), and sodium salt of imidazole (145 mg, 1.56 mmol) were placed in an eggplant-shaped flask (25 ml), and the mixture was stirred at 70° C. for 1.5 hours in an atmosphere of argon.

At the end of the reaction, the reaction mixture was poured into ice-cold water (5 ml) and extracted with diethyl ether (50 ml×1, 40 ml×1).

The extraction was extracted with ethyl acetate (250 mg×2). The ethyl acetate layers were washed with brine, and dried over anhydrous sodium sulfate.

The solvent was removed from the dried solution by evaporation under reduced pressure to obtain a crude product (592.5 mg).

The crude product was chromatographed on a silica gel column (dia. 2.5 cm×height 5.0 cm, 7 g) with ethyl acetate to obtain the title compound (Compound No. 54) 290.6 mg, 77.8%).

mp: 168°–170° C.

$^1$H-NMR (δppm, CDCl$_3$): 1.27 (s, 3H), 1.29 (s, 3H), 2.29 (d, 1H), 2.63 (m, 2H), 3.58 (dd, 1H), 3.80 (dd, 1H), 3.99 (d, 1H), 4.04 (d, 1H), 7.07 (s, 1H), 7.13 (s, 1H) 7.16 (d, 2H), 7.52 (d, 2H), 7.70 (s, 1H).

IR (V$_{max}$, cm$^{-1}$, KBr): 3200s, 2210s, 1605s, 1510s, 1220s, 1110s, 1080s, 1025s

EXAMPLE 5

[1] Synthesis of 2,2-dimethyl-4-carbomethoxy-4-(2-biphenylmethyl)-tetrahydrofuran-3-one (4-67).

n-Hexane washed sodium hydride (240 mg, 10 mmol) and tetrahydrofuran (10 ml) were placed in an eggplant-shaped flask (50 ml). 2,2-Dimethyl-4-carbomethoxytetrahydrofuran-3-one (5-67) (1.755 g, 10 mmol) was slowly dripped to the suspension at 0° C. Hydrogen gas was immediately generated.

The resulting light yellow solution was stirred at 0° C. for 10 minutes, followed by slowly adding 2-(bromomethyl)-biphenyl (2.595 g, 10.5 mmol). After the resulting solution was stirred at room temperature overnight, distilled water was added to the solution to cease the reaction.

The solution was extracted with ether (100 ml×1, 50 ml×1). The ether layers were washed with brine, dried over anhydrous sodium sulfate, and concentrated by using an evaporator to obtain a crude product (3.52 g). The crude product was purified by silica gel column chromatography using n-hexane-ethyl acetate (5:1), thus obtaining the title compound (4-67) (3.07 g, 91.0%).

$^1$H-NMR (δppm, CDCl$_3$): 0.82 (s, 3H), 1.19 (s, 3H), 3.21 (d, 1H), 3.52 (d, 2H), 3.67 (s, 3H), 4.17 (d, 1H), 7.2–7.3 (m, 6H), 7.36 (t, 1H), 7.42 (t, 2H).

[2] Synthesis of 2,2-dimethyl-4-(2-biphenylmethyl)-tetrahydrofuran-3-one (3-67)

The ketoester compound (4-67) (1.694 mg, 5.01 mmol), 12.5% sulfuric acid (5 ml), and acetic acid (10 ml) were placed in an eggplant-shaped flask (100 ml) and reacted at 130° C. for 8 hours. The reaction was ceased by pouring the solution into distilled water (50 ml) at 4° C.

The resulting solution was extracted with ether (50 ml×1, 30 ml×1). The ether layers were washed with a saturated aqueous solution of sodium hydrogencarbonate and with distilled water, and dried over magnesium sulfate.

The solvent was removed from the dried solution by using an evaporator to obtain a crude product (3-67) (1.354 g).

Rf: 0.521 (n-hexane-ethyl acetate=5:1).

$^1$H-NMR (δppm, CDCl$_3$): 0.994 (s, 3H), 1.083 (s, 3H) 2.42 (d, 1H), 2.62 (d, 1H), 3.49 (t, 1H) 3.76 (t, 1H), 7.2–7.3 (m, 6H), 7.3–7.4 (m, 3H).

IR (V$_{max}$, cm$^{-1}$, KBr): 3150m, 3125m, 2971m, 2925m, 2850m, 1740s

[3] Synthesis of 7-(2-phenylbenzyl)-4,4-dimethyl-1,5-dioxaspiro[2.4-]heptane (2-67)

Trimethylsulfonium iodide (1.430 g, 6.5 mmol) and DMSO (6 ml) were placed in an eggplant-shaped flask (50 ml).

n-Hexane-washed sodium hydride (156 mg, 6.5 mmol) was gradually added at 10° C., and the mixture was stirred at room temperature for 30 minutes.

A solution of the ketone compound (3-67) in DMSO (2.0 ml) was slowly added to the solution at 10° C., followed by stirring at room temperature for 1 hour.

After the end of the reaction had been confirmed, the solution was poured into ice-cold water to cease the reaction. The solution was extracted with ether (50 ml×1, 30 ml×1). The ether layers were washed with distilled water (30 ml), and then washed with brine (30 ml×1). The washed solution was dried over anhydrous sodium sulfate and concentrated under reduced pressure, thus obtaining a crude product of the title compound (2-67) (881.9 mg).

[4] Synthesis of 2,2-dimethyl-3-(1H-1,2,4-triazol-1-ylmethyl)-3-hydroxy-5-(2-phenylbenzyl)-tetrahydrofuran (Compound No. 67)

The epoxide compound (2-67) (881.9 mg. 3.34 mmol), sodium salt of 1H-1,2,4-triazole (394.9 mg, 4.34 mmol), and dimethylformamide (5.0 ml) were placed in an eggplant-shaped flask (100 ml).

The mixture was stirred at 70° C. for 2 hours in an atmosphere of argon, poured into cold water, and extracted with ether (100 ml×1, 50 ml×1). The ether layers were washed with distilled water and brine, and then dried over anhydrous sodium sulfate.

The dried solution was concentrated by using an evaporator to obtain a crude product (794.1 mg).

The crude product was recrystallized from ethyl acetate-n-hexane to obtain the title compound as white crystals (Compound No. 67) (469 mg).

Rf: 0.42 (n-hexane-ethyl acetate=1:4). mp: 150°–151° C.

$^1$H-NMR 0.64 (s, 3H), 1.07 (s, 3H), 2.25 (m, 1H), 2.65 (dd, 1H), 2.85 (dd, 1H), 3.50 (t, 1H), 3.64 (t, 1H), 3.71 (d, 1H), 3.76 (d, 1H), 7.32 (m, 9H), 7.89 (s, 1H), 8.00 (s, 1H)

IR (V$_{max}$, cm$^{-1}$, KBr): 3425W, 3150s, 2980s, 2900s, 1600w, 1520s, 1482s, 1440s, 1423m, 1365m, 1280s, 1202m, 1130s

[5] Synthesis of 2,2-dimethyl-3-(imidazol-1-ylmethyl)-3-hydroxy-5-(2-phenylbenzyl)-tetrahydrofuran (Compound No. 68)

The epoxide compound (2-67) (9.21 mg, 3.49 mmol), sodium salt of imidazole (453 mg, 4.53 mmol), and dimethylformamide (5.0 ml) were placed in an eggplant-shaped flask (100 ml), and the mixture was heated and maintained at 70° C. for 2.5 hours in an atmosphere of argon.

The solution was poured into cold water (50 ml) and extracted with ether (100 ml×1, 50 ml×1). The ether layers were washed with brine and dried over anhydrous sodium sulfate. The dried solution was concentrated under reduced pressure to obtain a crude product (930.5 mg).

The crude product was recrystallized from n-hexane-ethyl acetate to obtain the title compound as white crystals (Compound No. 68) (781.8 mg, 69%).

Rf: 0.24 (ethyl acetate) mp: 92°-95° C.

$^1$H-NMR (δppm, CDCl$_3$): 0.71 (s, 3H), 1.05 (s, 3H), 2.30 (m, 1H), 2.60 (dd, 1H), 2.82 (dd, 1H), 3.42 (d, 1H), 3.60 (d, 1H), 6.91 (s, 1H), 6.98 (s, 1H); 7.27 (m, 9H).

IR (V$_{max}$, cm$^{-1}$, KBr): 3450m, 3200m, 3000m, 2950m, 2890m, 1600w. 1520s, 1484m, 1440m.

EXAMPLE 6: ACUTE TOXICITY

Acute toxicity by oral route was investigated using ICR-JCL mice

The compounds of the present invention, Compound Nos. 1, 2, 13, 14, 33, 34, 41, 42, 47, 48, 53, 54, 67, and 68, were dissolved or dispersed in polyethylene glycol 200 or physiological saline. The solution or suspension was given in a prescribed amount by means of a syringe or a stomach tube. After administration, intoxication symptoms were observed for 7 consecutive days to determine lethality and to calculate the LD$_{50}$ value, which was more than 1000 mg/kg for each compound of the present invention.

EXAMPLE 7: ANTIMYCOTIC ACTIVITY

Five-week-old female ICR mice of 10 animals per group were infected with *Candida albicans* (IFO 1060) in an amount of 4.8×10$^6$ cfu (colony forming unit)-/mouse through a tail vein.

After one hour following the introduction of the infection, a solution of each compound (see Table 8 below) in polyethylene glycol 200 was orally administered for 5 consecutive days in the amount of 100 mg/kg day.

After the end of the administration, mortality was observed for 20 days and the survival rate and mean survival days were calculated.

The results are shown in Table 8. In Table 8, the solvent group was administered only with polyethylene glycol.

TABLE 8

| Comp. No. | Survival Rate (%) |
|---|---|
| 1 | 40 |
| 2 | 55 |
| 13 | 55 |
| 14 | 70 |
| 21 | 37 |
| 22 | 46 |
| 33 | 60 |
| 34 | 80 |
| 41 | 56 |
| 42 | 63 |
| 47 | 58 |
| 48 | 53 |
| 53 | 42 |
| 54 | 40 |
| 67 | 53 |
| 68 | 62 |
| Control | 20 |
| Solvent Control | 20 |

EXAMPLE 8: AROMATASE INHIBITORY ACTIVITY

Aromatase activity was determined in the manner described by Covey, D. F., Biochem. Biophys. Res. Commun. 157 (1), 81-86 (1988).

Aromatase inhibitory activity of the compounds was evaluated in the 50% aromatase-inhibitory concentration (IC$_{50}$). Microsomes of human placenta and [19-$^{14}$C]4-androstene-3,17 dione were used as an aromatase source and a substrate, respectively.

The radioactivity of H$^{14}$COOH which was released into a reaction mixture as a result of aromatization was measured to evaluate the aromatase activity.

The aromatase inhibitory activity and the concentration of each compound was depicted in a graph, from which the IC$_{50}$ was determined.

[19-$^{14}$C]4-Androstene-3,17-dione (1×10$^{-6}$M, 2 KBq/ml), human placenta microsomes (a protein concentration of 0.1 coenzyme NADP (2×10$^{-3}$M), glucose-6-phosphoric acid (4×10$^{-3}$M), and glucose-6-phosphoric acid dehydrogenase (4U/ml) were added to a phosphoric acid buffer solution (67 mM, pH 7.2, 0.5 ml) and reacted at 37° C. for 30 minutes while the mixture was being shaken.

The test compound dissolved in DMSO was added to the reaction mixture and the final concentration of DMSO was in the range of 0.1 to 0.55% by volume per volume.

Chloroform (5 ml) was then added to the reaction mixtures to cease the reaction. The H$^{14}$COOH, which had been released into a reaction mixture, was recovered in a water layer by stirring the reaction mixture. The water layer (0.1 ml) was added to a liquid scintillation cocktail (Atomlight, Dupont, 4 ml) to measure its radioactivity.

The results are shown in Table 9. The positive control is 4-hydroxyandrostenedione.

TABLE 9

| Comp. No. | IC$_{50}$ (M) |
|---|---|
| 1 | 6.0 × 10$^{-6}$ |
| 2 | 5.3 × 10$^{-7}$ |
| 13 | 5.3 × 10$^{-6}$ |
| 14 | 4.8 × 10$^{-7}$ |
| 21 | 4.7 × 10$^{-6}$ |
| 22 | 6.3 × 10$^{-7}$ |
| 33 | 7.0 × 10$^{-6}$ |
| 34 | 5.0 × 10$^{-7}$ |
| 41 | 3.0 × 10$^{-6}$ |
| 42 | 2.7 × 10$^{-7}$ |
| 47 | 1.0 × 10$^{-6}$ |
| 48 | 1.5 × 10$^{-6}$ |
| 53 | 1.2 × 10$^{-6}$ |
| 54 | 1.0 × 10$^{-6}$ |
| 67 | 4.7 × 10$^{-6}$ |
| 68 | 3.5 × 10$^{-7}$ |
| Positive Control | 2.0 × 10$^{-5}$ |

EXAMPLE 9: ANTITUMOR EFFECTS

Fifty-day-old female Sprague-Dawley rats were orally given 7,12-dimethylbenzanthracene (15 mg/kg) and observed for two months. Those rats developing spontaneous mastocarcinoma were selected and divided into groups each consisting of 15 animals: groups each of which is to be given a different compound of the present invention; a group to be given a control compound; and a control group to be given a simple physiological saline solution. Each group was intraperitoneally given the corresponding physiological saline solution or dispersion in an amount of 25 mg/kg daily for 20 consecutive days. Five days after the last administration, the rats were sacrificed to weigh the tumors. The mean tumor weight (T) of the 15 rats of each of the groups which had been given compounds of the present invention or the control compound, and the mean tumor weight (C) of the 15 rats of the control group which had been given a simple physiological saline solution were calculated. The tumor growth inhibition rate of each group was calculated on the basis of the following formula:

Tumor Growth Inhibition Rate $(\%)=\{1-T/C\}\times 100$. The results are shown in Table 10. Positive control is 4-hydroxyandrostenedione.

TABLE 10

| Comp. No. | Inhibition rate (%) |
| --- | --- |
| 1 | 60 |
| 2 | 54 |
| 13 | 58 |
| 14 | 63 |
| 21 | 72 |
| 22 | 75 |
| 33 | 65 |
| 34 | 80 |
| 41 | 48 |
| 42 | 56 |
| 47 | 55 |
| 48 | 70 |
| 53 | 60 |
| 54 | 73 |
| 67 | 74 |
| 68 | 85 |
| Positive Control | 48 |

EXAMPLE 10: PREPARATION OF FORMULATION

| | |
| --- | --- |
| Compound No. 1 | 100 mg |
| Polyoxyethylene Sorbitan Mono-oleate | 50 mg |
| Starch Powder | 250 mg |

The above ingredients were mixed uniformly and put into a capsule, thus preparing a capsule containing 100 mg of Compound No. 1.

What is claimed is:

1. An azole derivative of the formula:

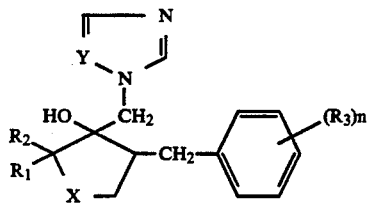

(I)

including stereoisomers thereof, wherein $R_1$ and $R_2$ each are H or $C_1$–$C_4$ alkyl; $R_3$ is H, OH, CN, halogen, halo $C_1$–$C_4$ alkyl, $C_1$–$C_4$ alkyl, or phenyl, and if there are two or more $R_3$ groups, such $R_3$ groups may be the same or different; n is an integer from 0 to 5; Y is CH; and X is O, S, or NH; or a pharmaceutically acceptable salt thereof.

2. The azole derivative of claim 1 wherein $R_1$ and $R_2$ each are H, methyl, ethyl, n-propyl, i-propyl, n-butyl, or t-butyl; $R_3$ is halogen, CN, or phenyl; n is an integer from 0 to 2; and X is O, S, or NH.

3. A pharmaceutical composition comprising an antimycotic effective amount of an azole derivative of claim 1 and a pharmaceutically acceptable carrier or diluent.

4. A method of treating mycosis comprising administering to a patient in need thereof a mycosis treating effective amount of an azole derivative of claim 1.

* * * * *

UNITED STATES PATENT AND TRADEMARK OFFICE
CERTIFICATE OF CORRECTION

PATENT NO.  : 5,324,740
DATED       : June 28, 1994
INVENTOR(S) : Koichi NIIMURA et al.

It is certified that error appears in the above-indentified patent and that said Letters Patent is hereby corrected as shown below:

Column 5, compound (IIA) should be depicted as

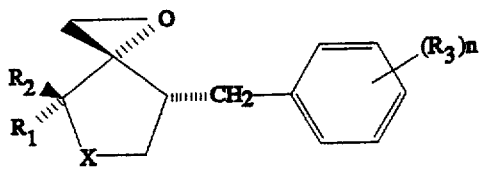

and compound (IIB') should be depicted as

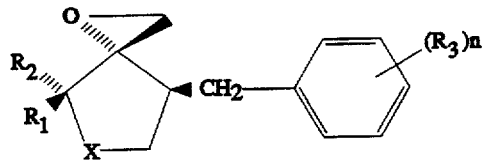

Column 8, "Comp. No. 30" (second occurrence) should read --Comp. No. 40--.

Signed and Sealed this

Fourth Day of April, 1995

*Attest:*

BRUCE LEHMAN

*Attesting Officer*     *Commissioner of Patents and Trademarks*